United States Patent [19]

West et al.

[11] 4,183,741
[45] Jan. 15, 1980

[54] HERBICIDALLY-ACTIVE HETEROCYCLIC COMPOUNDS

[75] Inventors: Peter J. West, Cambridge; John H. Parsons, Saffron Walden, both of England

[73] Assignee: Fisons Limited, London, England

[21] Appl. No.: 799,127

[22] Filed: May 20, 1977

[30] Foreign Application Priority Data

May 21, 1976 [GB] United Kingdom ............... 20982/76
Nov. 26, 1976 [GB] United Kingdom ............... 49326/76

[51] Int. Cl.² .................... A01N 9/02; A01N 9/22; C07D 471/22
[52] U.S. Cl. ........................ 71/92; 546/119; 546/64; 544/343
[58] Field of Search ............ 260/250 BC; 71/92; 544/343; 546/64

[56] References Cited

U.S. PATENT DOCUMENTS

| 3,594,479 | 7/1971 | Maguire et al. | 260/250 BC |
| 3,629,260 | 12/1971 | Maguire et al. | 260/250 BC |
| 4,044,015 | 8/1977 | Kuhla | 260/250 BC |

Primary Examiner—Donald G. Daus
Assistant Examiner—James H. Turnipseed
Attorney, Agent, or Firm—Wenderoth, Lind & Ponack

[57] ABSTRACT

There are provided the compounds of the formula:

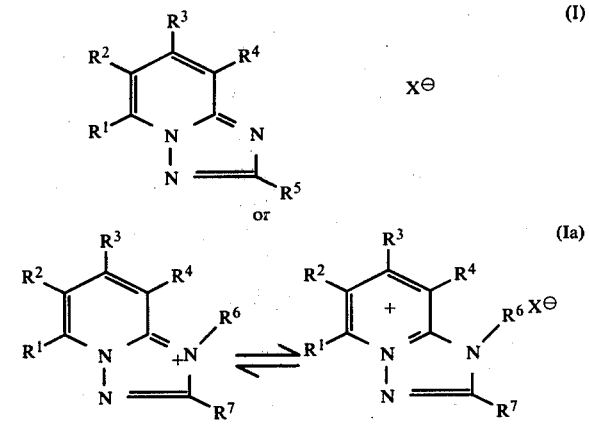

(wherein $R^1$, $R^2$, $R^3$ and $R^4$, which may be the same or different, each represent hydrogen, a substituted or unsubstituted alkyl, aryl or aralkyl group, a nitro group, a cyano group or a halogen atom, $R^5$ represents a quaternized nitrogen-containing heterocyclyl radical linked via a ring carbon atom, X represents one equivalent of an anion, $R^7$ represents a substituted or unsubstituted alkyl group or a substituted or unsubstituted, saturated or unsaturated heterocyclyl group which, if nitrogen-containing, is quaternized, linked via a ring carbon atom, and $R^6$ either represents an alkyl group or, when $R^7$ represents a quaternized nitrogen-containing heterocyclyl group, and the quaternized nitrogen atom is ortho to the linked ring carbon atom, may represent a methylene, dimethylene, trimethylene or alkyl-substituted ethenylene chain to that nitrogen atom.

The compounds are selective herbicides.

11 Claims, No Drawings

HERBICIDALLY-ACTIVE HETEROCYCLIC COMPOUNDS

This invention concerns compounds which are active on plant physiology, compositions containing said compounds, and methods of using said compounds.

In one aspect, this invention provides the s-triazolo[1,5-a]pyridine salts of the formula:

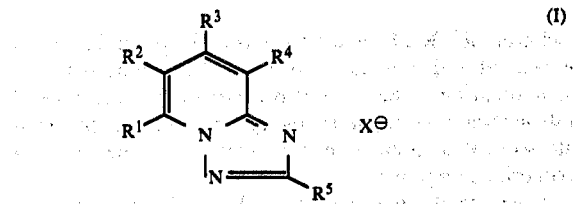

and the s-triazolo[1,5-a]pyridinium salts of the formula:

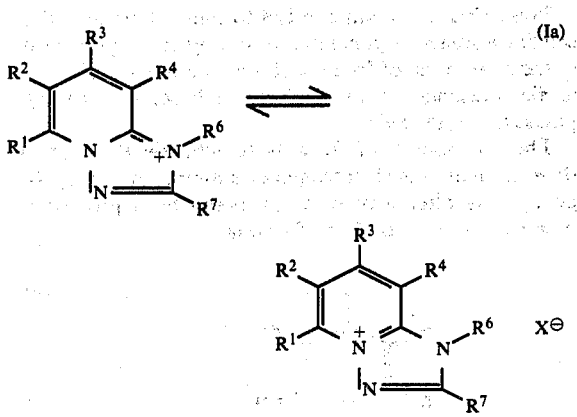

(wherein $R^1$, $R^2$, $R^3$ and $R^4$, which may be the same or different, each represent hydrogen, an alkyl, aryl or aralkyl group, each of which may be substituted or unsubstituted, a nitro group, a cyano group or a halogen atom, $R^5$ represents a quaternised nitrogen-containing heterocyclyl radical liked via a ring carbon atom, X represents one equivalent of an anion, $R^7$ represents a substituted or unsubstituted alkyl group, or a substituted or unsubstituted, saturated or unsaturated heterocyclyl group (which, if nitrogen-containing, is quaternised) linked via a ring carbon atom, and $R^6$ either represents an alkyl group or, when $R^7$ represents a quaternised nitrogen-containing heterocyclyl group and the quaternised nitrogen atom is ortho to the linked ring carbon atom, may represent a methylene, dimethylene, trimethylene or alkyl-substituted ethenylene chain to that nitrogen atom.

Preferably at least two of $R^1$, $R^2$, $R^3$ and $R^4$ represent hydrogen. Again preferably, at least one of $R^1$, $R^2$, $R^3$ and $R^4$ represents halogen, especially chlorine or bromine. Again preferably, at least one of $R^1$, $R^2$, $R^3$ and $R^4$ represents a substituted or unsubstituted alkyl group. When one or more of $R^1$, $R^2$, $R^3$ and $R^4$ represents a substituted or unsubstituted alkyl group, it is preferably such a group containing from 1 to 6 carbon atoms, for example methyl, ethyl, n-propyl, isopropyl or n-butyl, preferably unsubstituted, but the or each substituent thereon, where present, being preferably a halogen atom, for example chlorine or bromine. Methyl is especially preferred. Preferred aryl and aralkyl groups which $R^1$, $R^2$, $R^3$ and $R^4$ may represent are phenyl and C 7 to 10 aralkyl, e.g. benzyl, preferably unsubstituted, but optionally substituted by one or more halogen atoms, for example chlorine or bromine, or alkyl groups, especially of 1 to 6 carbon atoms, for example methyl or ethyl.

$R^5$ preferably represents an unsaturated heterocyclyl radical, which is substituted on the quaternised nitrogen atom by a C 1 to 6 alkyl group which may be unsubstituted or substituted (especially by cyano, carboxy or C 1 to 6 alkoxycarbonyl) or a C 2 to 6 alkenyl or alkynyl group, for example methyl, ethyl, vinyl or ethynyl. Preferred groups are 5- or 6- membered, especially pyridinium groups, for example 1-methylpyridinium-4-yl, 1-ethoxycarbonyl-methylpyridinium-4-yl, or 1-cyanomethylpyridinium-4-yl.

$R^6$ preferably represents either an alkyl group having from 1 to 6 carbon atoms, for example methyl, ethyl, n-propyl, iso-propyl or n-butyl, or a dimethyhlene, trimethylene or alkyl-substituted ethylene chain to a quaternised nitrogen atom or an appropriate group $R^7$.

$R^7$ preferably represents an unsubstituted heterocyclyl group or a heterocyclyl group substituted by a group $R^9$ where $R^9$ represents a substituent group, e.g. C 1 to 6 alkyl or substituted (especially by cyano, carboxy or C 1 to 6 alkoxycarbonyl) alkyl, C 2 to 6 alkenyl or alkynyl, or C 7 to 10 aralkyl, e.g. benzyl, $R^7$ preferably represents a quaternised nitrogen-containing aromatic heterocyclyl group, particularly a 5- or 6-membered group, and especially a pyridinium group, for example 1-methylpyridinium-4-yl, 1-ethoxycarbonylmethyl-pyridinium-4-yl, 1-cyanomethylpyridinium-4-yl or pyridinium-2-yl. When, however, $R^7$ represents a substituted or unsubstituted alkyl group, it is preferably such a group having from 1 to 6 carbon atoms, for example methyl, ethyl, n-propyl, iso-propyl or n-butyl. When $R^7$ represents a substituted alkyl group, the or each substituent thereon is preferably a halogen atom, for example chlorine or bromine.

$X^-$ may for example, represent $Cl^-$, $Br^-$, $I^-$, $NO_3^-$, $\frac{1}{2}SO_4^{2-}$, $ClO_4^-$, $\frac{1}{3}PO_4^{3-}$, $BF_4^-$, $FSO_3^-$, $CH_3COO^-$, $OH^-$, $CO_3^{2-}$, $HCO_3^-$, $Br_3^-$, $I_3^-$, $RSO_3^-$ where R represents an alkyl, aryl, alkoxyaryl or alkylaryl group, or $RSO_4^-$ where R represents an alkyl group, e.g. methyl. Preferably, although the plant physiological activity of the compounds of the present invention lies not in the anion, for convenience $X^-$ represents $Cl^-$, $Br^-$, $I^-$ or $CH_3SO_4^-$.

When $R^7$ represents a quaternised nitrogen-containing heterocyclyl radical, two equivalents of anion must be present, which may be the same or different.

This invention naturally extends to the various tautomeric forms which exist of the compounds of formulae I and Ia.

Particularly preferred compounds of formulae I and Ia are 1-methyl-2-(1-methylpyridinium-4-yl)-s-triazolo[1,5-a]pyridinium salts, 6,7-dihydropyrido[1,2-a]pyrido[1',2'-1,5]-s-triazolo [3,4-c]pyrazinediium salts, 6,7-dihydro-10-methylpyrido[1,2-a]pyrido[1',2'-1,5]-s-triazolo[3,4-c]pyrazinediium salts and 11-chloro-6,7-dihydropyrido[1,2-a]pyrido[1',2'-1,5]-s-triazole[3,4-c]pyrazinediium salts, especially the bis(methyl sulphate) of the first and the dibromide of the others. Other preferred compounds are those prepared in the Examples provided hereinafter.

In another aspect, this invention provides a process for the preparation of an s-triazolo[1,5-a]pyridinium salt of formula Ia as defined hereinbefore, wherein $R^6$ represents an alkyl group, in which a compound of the formula:

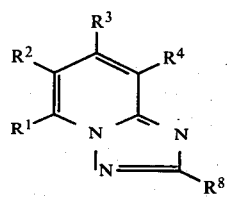

(Ic)

(wherein $R^1$, $R^2$, $R^3$, and $R^4$ are as defined hereinbefore, and $R^8$ represents a substituted or unsubstituted alkyl group or a substituted or unsubstituted, saturated or unsaturated, quaternised or unquaternised heterocyclyl group linked via a ring carbon atom) is reacted with a compound of formula $R^{10}X$ (wherein $R^{10}$ represents an alkyl group as defined for $R^6$ and X is as defined hereinbefore) to give the corresponding compound of formula Ia.

The reaction is preferably effected at from 10° C. to reflux, especially at 70°–120° C., optionally in the presence of a suitable solvent, e.g. an alkanol, e.g. methanol, or a ketone, e.g. methyl ethyl ketone.

In a further aspect, this invention provides a process for the preparation of an s-triazolo[1,5-a]pyridinium salt of formula Ia as defined hereinbefore wherein $R^6$ represents a methylene, dimethylene or trimethylene group, in which a compound of formula Ic as defined hereinbefore wherein $R^8$ represents a nitrogen-containing heterocyclyl group, the or a nitrogen atom of which is ortho to the linked ring carbon atom, is reacted with a compound of formula $X.R^{11}.X$ (wherein $R^{11}$ represents methylene, dimethylene or trimethylene, and each X is as defined hereinbefore).

X preferably represents bromine.

The compound $X.R^{11}.X$ usually acts as solvent for the reaction. Other solvents may be present if desired, however. The reaction is conveniently carried out at from 70° C. to reflux (up to about 130° C.).

In a further aspect, this invention provides a process for the preparation of an s-triazole[1,5-a]pyridinium salt of formula Ia as defined hereinbefore wherein $R^6$ represents an ethenylene group, in which a compound of formula Ic as defined hereinbefore wherein $R^8$ represents a nitrogen-containing heterocyclyl group, the or a nitrogen atom of which is ortho to the linked ring carbon atom, is reacted with a halomethylketone of formula $HalCH_2COR$, where Hal represents a halogen, e.g. chlorine, and R represents alkyl, especially C 1 to 6 alkyl, e.g. methyl to give the corresponding compound the nitrogen atom on the group $R^8$ of which is quaternised by a group —$CH_2COR$, which is then halogenated and cyclised to give the corresponding compound of formula 1a wherein $R^6$ represents ethenylene, substituted by a group R. The reaction with the halomethylketone is preferably effected at from 10° C. to reflux, especially at 70° C. to 120° C., optionally in the presence of other solvents, e.g. a ketone, e.g. methylethylketone. The halogenation and cyclisation is conveniently effected by heating in phosphorus trichloride to from 70° C. to 140° C., especially at reflux.

The compounds of formula Ic wherein $R^8$ is other than a quaternised nitrogen-containing heterocyclyl group, employed as starting materials in the above process, may themselves be prepared by a process in which a compound of the formula:

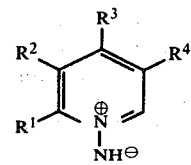

(II)

(wherein $R^1$, $R^2$, $R^3$ and $R^4$ are as defined hereinbefore) is reacted with a nitrile of formula $R^8CN$ (wherein $R^8$ is as defined hereinbefore but is other than a quaternised nitrogen-containing heterocyclyl group) in an appropriate solvent medium which is inert under the reaction conditions employed.

The solvent medium employed is preferably an aqueous alkanol, for example an ethanol/water mixture, and the reaction is preferably effected at 10° C.-reflux, especially at 10° C. to 40° C.

Preferably, the compound of formula II employed as starting material is generated in situ by employing a salt of the compound of formula II, for example the chloride in the presence of an alkali-metal base, for example potassium hydroxide.

The compounds of formula Ic wherein $R^8$ is other than a quaternised nitrogen-containing heterocyclyl group may alternatively be prepared by a process in which a compound of the formula:

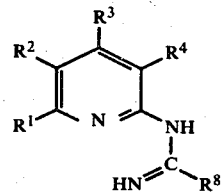

(III)

(wherein $R^1$, $R^2$, $R^3$, $R^4$ and $R^8$ are as defined hereinbefore with the proviso that $R^8$ is other than a quaternised nitrogen containing heterocyclyl group) is cyclised in the presence of an oxidising agent to give the corresponding compound of formula Ic.

The oxidising agent may be any convenient oxidising agent for effecting the cyclisation. Preferably, however, it is a halogen, especially chlorine, an alkali-metal hypochlorite, especially sodium hypochlorite, or lead tetraacetate. A solvent, e.g. an aqueous alkanol, for example methanol, is preferably employed, and the temperature is desirably maintained below 15° C.

The compounds of formula III used as starting materials in the above process may be prepared by a process in which an aminopyridine of the formula:

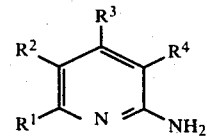

(IV)

(wherein $R^1$, $R^2$, $R^3$ and $R^4$ are as defined hereinbefore) is reacted with a nitrile of formula $R^8CN$, where $R^8$ is as defined hereinbefore but is other than a quaternised nitrogen-containing heterocyclyl group, to give the corresponding compound of formula III.

The reaction is conveniently effected especially at 70° to reflux in a non aqueous solvent, and advantageously in the presence of a base, e.g. an alkali-metal alkoxide, e.g. sodium ethoxide. The solvent is preferably an alkanol which, when an alkali-metal alkoxide is employed, preferably corresponds to the alkoxide employed.

The compounds of formula Ic wherein $R^8$ is other than a quaternised nitrogen-containing heterocyclyl group may alternatively be prepared by a process in which a compound of formula:

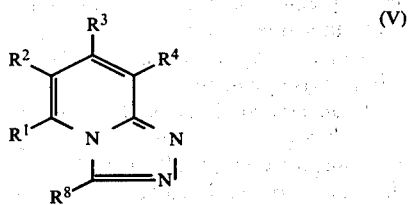

(wherein $R^1$, $R^2$, $R^3$, $R^4$ and $R^8$ are as defined hereinbefore with the proviso that $R^8$ is other than a quaternised nitrogen-containing heterocyclyl group) is isomerised in the presence of a base to give the corresponding compound of formula Ic.

The reaction is desirably carried out in an appropriate solvent medium, e.g. an aqueous alkanol, e.g. aqueous ethanol.

The base is preferably an alkali-metal hydroxide, e.g. sodium hydroxide, and the reaction is desirably effected at 10° C. to 80° C.

The present invention extends to the compounds of formula I or Ia whenever prepared by a process as described herein.

The compounds of formula Ic wherein $R^8$ represents a nitrogen-containing heterocyclyl group (i.e. compounds of formula I) may be prepared by a process in which a corresponding compound of formula Ic wherein $R^8$ represents a non-quaternised nitrogen-containing heterocyclyl group is reacted with a quaternising agent of formula $R^9X$ wherein $R^9$ and X are as defined hereinbefore in an appropriate solvent medium which is inert under the reaction conditions employed.

The solvent medium may, for example, be an alkanol, for example of 1 to 6 carbon atoms, e.g. methanol or ethanol.

The present compounds are active on plant physiology, and may be used as herbicides. They are particularly effective against barnyardgrass (*echinochloa crusgalli*), crabgrass (*digitaria sanguinalis*) and pigweed (*amaranthus retroflexus*), and also possess activity against yellow nutsedge (*cyperus esculentus*), couch grass (*agropyron repens*), wild oats (*avena fatua*) and blackgrass (*alopecurus myosuroides*). The present compounds are in general active against monocotyledonous weeds whilst being relatively inactive against dicotyledonous crop species, for example cotton, rice, beans (for example soya beans, navy beans, haricot beans, French beans, runner beans and broad beans) wheat, groundnuts and peas.

In a further aspect, this invention provides a method of combating weeds at a locus infested with or liable to be infested with them, which method comprises applying to said locus a herbicidally-effective amount of one or more compounds of formula I of formula Ia as defined hereinbefore.

The present compounds are normally employed in the form of compositions, which can be prepared by admixing the ingredients. Usually the compositions are initially produced in the form of concentrates, e.g. containing 0.5 to 99%, especially 0.5–85% of the present compounds, and these are diluted with water or hydrocarbon, usually water, for application, generally such that the concentration of the compounds is 0.05–5%. Percentages and parts in this specification are by weight unless otherwise indicated.

The compositions normally contain a surface active agent and/or a carrier.

The carrier may be a liquid, e.g. water (e.g. water used to dilute a concentrate for application). If water is employed as carrier in a concentrate, an organic solvent may also be present as carrier, though this is not usually employed. A surface active agent may advantageously be present.

Many of the compounds are soluble in water and may be used most advantageously as aqueous solutions with or without a surface active agent.

The carrier may be a liquid other than water, for example an organic solvent, such as a water immiscible solvent, e.g. a hydrocarbon which boils within the range 130°–270° C., in which the compound is dissolved or suspended. A concentrate containing a water immiscible solvent suitable also contains a surface active agent so that the concentrate acts as a self-emulsifiable oil on admixture with water. The liquid may be a water-miscible solvent e.g. 2-methoxy ethanol, methanol, propylene glycol, diethylene glycol, diethylene glycol monoethyl ether, formamide or methylformamide.

The carrier may be a solid, which may be finely divided. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be a modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant e.g. a polyhalogenated alkane such as dichlorodifluoromethane, and suitably also with a solvent.

A flowable suspension concentrate may be formed by grinding the compound with water, a wetting agent and a suspending agent.

Thus the present composition can for example be solid (e.g. dust or granules) and contain a solid carrier or liquid (e.g. an emulsifiable concentrate) and contain a liquid carrier which is a hydrocarbon which boils within the range 130°–270° C.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with fatty alcohol ethoxylates or salts of such esters, fatty alcohol sulphates such as sodium dodecyl sulphate, ethoxylated fatty alcohol sulphates, ethoxylated alkylphenol sulphates, lignin sulphonates, petroleum sulphonates, alkylaryl sulphonates such as alkyl-benzene sulphonates or lower alkyl-naphthalene sulphonates, salts of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl taurine or the dialkyl sulphosuccinates e.g. the sodium sulphonate of dioctyl succinate.

The surface active agents may also comprise nonionic agents, for example condensation products of fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quarternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, sodium oleoyl N-methyltauride, dialkyl sulphosuccinates, alkyl phenol ethoxylates, and fatty alkyl ethoxylates.

The present active compounds and particularly the 1-methyl-2-(1-methylpyridinium-4-yl)-s-triazolo[1,5-a]pyridinium salts, the 6,7-dihydropyrido[1,2-a]pyrido[1',2'-1,5]-s-triazolo[3,4-c] pyrazinediium salts, the 6,7-dihydro-10 -methylpyrido[1,2-a]pyrido [1',2'-1,5]-s-triazolo[3,4-c]pyrazinediium salts and the 11-chloro-6,7-dihydropyrido[1,2-a]pyrido[1',2'-1,5]-s-triazolo [3,4-c]pyrazinediium salts, may be admixed with another pesticide, e.g. herbicide, insecticide or fungicide, or with a plant growth regulant or with a fertilizer. Particular advantages are obtained with mixtures with a second herbicide. The present compounds may be used sequentially with a second herbicide, e.g. one herbicide applied before planting or before emergence of a crop and the other herbicide applied after emergence of the crop.

The second herbicide employed in admixture or sequentially with the compounds of the present invention may be, for example, a substituted benzofuran herbicide, a phenoxyaliphatic acid, substituted urea, triazine phenol, nitrile, bipyridylium compound, substituted benzoic acid, halogenated aliphatic acid, carbamate, thiocarbamate, chloroacetamide, diazine, arsenic compound or other herbicidal compound. In respect to selective herbicidal compositions for post-emergence use, the second herbicide is preferably a substituted phenoxyaliphatic acid; in respect of selective herbicidal compositions for pre-emergence use, the second herbicide is preferably a substituted benzofuran, a substituted urea or triazine.

The substituted benzofuran herbicide is preferably a compound of the formula:

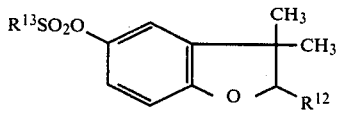

where $R^{12}$ represents alkoxy (especially ethoxy, propoxy or isopropoxy), and $R^{13}$ represents alkyl (especially methyl) or a group $R^{14}R^{15}N-$ where $R^{14}$ and $R^{15}$, which may be the same or different, each represent hydrogen, alkyl (especially methyl) or carboxylic acyl (especially acetyl).

Particularly preferred substituted benzofuranyl compounds for admixture with the compounds of the present invention, especially with those specifically identified herein, 2-ethoxy-2,3-dihydro-3,3-dimethylbenzofuran-5-yl methanesulphonate (common name ethofumesate);

2-ethoxy-2,3-dihydro-3,3-dimethylbenzofuran-5-yl methylsulphamate; and 2-ethoxy-2,3-dihydro-3,3-dimethylbenzofuran-5-yl dimethylsulphamate.

The phenoxyaliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or may be of only slight herbicidal activity. Examples The substituted urea generally comprises a tri- or tetra-substituted urea.

The triazine herbicide generally comprises a compound of the formula:

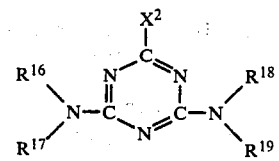

where $X^2$ is a halogen, $OY^1$ group or $SY^1$ group, where $Y^1$ is an alkyl group, and $R^{16}$, $R^{17}$, $R^{18}$, $R^{19}$ are hydrogen or alkyl.

Specific compounds with which the compounds of the present invention, especially those specifically identified herein, may be admixed are as follows, all common names being as set out in the Pesticide Manual, 4th edition, issued by the British Crop Protection Council:

alachlor, allidochlor, ametryne, aminotriazole (ATA), ancymidol, asulam, atrazine, aziprotryne, barban, benazolin, benfluralin, bensulide, bentazon, benthiocarb, bentranil, benzadox, benzoylprop-ethyl benzthiazuron, bifenox, bromacil, bromofenoxim, bromoxynil, bromoxynil octanoate, brompyrazone, butachlor, buturon, butylate, cabetamide, chinonamid, chloramben, chloranocryl, chlorburomuron, chlorbufam, chlorfenac, chlorfenprop-methyl, chlorflurecol-methyl, chlormequat, chloroxuron, chlorphonium, chlorpropham, chlorthal-dimethyl, chlorthiamid, chlortoluron, credazine, cyanazine, cycloate, cycluron, cyprazine, 2,4-D, dalapon, dalapon sodium, daminozide, 2,4-DB, delachlor, desmedipham, desmetryne, diallate, dicamba, dichlobenil, dichlorprop, dimethametryn, difenzoquat, difenzoquat methylsulphate, dimexan, dinitramine, dinoseb, dinoseb acetate, dinoterb, dinoterb acetate, diphenamid, dipropetryn, diquat, diuron, DNOC, DSMA, endothal, EPTC, erbon, ethiolate, EXD, fenoprop, fenuron, flamprop-isopropyl, fluometuron, fluorodifen, flumezin, flurecol-butyl, glyphosate, hexaflurate, ioxynil, ioxynil octanoate, isonoruron, isopropalin, isoproturon, karbutilate, lenacil, linuron, MCPA, MCPB, mecoprop, medinoterb acetate, merphos, methabenzthiazuron, methazole, methoprotryne, metobromuron, metoxuron, metribuzin, molinate, monalide, monolinuron, monuron, monuron-TCA, MSMA, napropamide, naptalam, neburon, nitralin, nitrofen, norflurazon, noruron, oryzalin, paraquat, pebulate, pentanochlor, phenmedipham, phenmedipham-ethyl, phenobenzuron, picloram, piperophos, profluralin, prometon, prometryne, propachlor, propanil, propazine, propham, propyzamide, pyrazon, secbumeton, siduron, simazine, simetryne, sulfallate, swep, 2,4,5-T, 2,3,6-TBA, TCA, terbacil, terbucarb, terbumeton, terbuthylazine, terbutryne, thiafluron, triallate, trietazine, trifluralin, and vernolate, N-(α,α-dimethylbenzyl)-N'-p-tolylurea, 3,4,5-tribromo-N,N-dimethylpyrazole-1-acetamide (U 27267), N-methyl-N-cyclohexyldithio-N'-o-fluorophenyl urea, N-benzoyl-N-(3,4-dichlorophenyl)-N',N'-dimethyl urea, ethyl-N,N-diisobutylthiolcarbamate, 4-(methylsulphonyl)-2,6-dinitro-N,N-dipropylaniline, 5-(6)-chloro-2-isopropylbenzimidazole, 1-(3,4-dichlorophenyl)-3-methyl-2-pyrrolidinone, N-(p-bromophenyl-N'-methyl-N'-methoxyurea, 3-(2,4-dichlorophenyl)-5-t-butyl-1,3,4-oxadiozol-2-one, N-(3,4-dichlorophenyl)-cyclopropanecarboxamide, 2,3,5-trichloro-4-pyridinol, 2-chloro-isopropylacetanilide, 2,6-dichlorothiobenzamide, 1,1'-bis(3,5-dimethylmorpholinocarbonylmethyl)-4,4'-bipyridilium, dichloride, sodium cis-3-chloroacrylate, 4,5,7-trichlorobenzthiadiazole-2,1,3, N-(3-chloro-4-methylphenyl)-2-methylpentanamide, n-propyl ethyl-n-butylthiolcarbamate, 3,4-dichloropropionanilide, N-cyclooctyl-N',N'-dimethylurea, butyl m-chlorophenylcarbamate, 2-chloro-N-(1,3-dioxolan-2-ylmethyl)-2',6'-dimethylacetanilide, tetrahydrofurfuryl isothiocyanate, N-chloroacetyl-N-(2,6-diethylphenyl)-glycine, isopropyl ester, N-chloroacetyl-N-(2,6-diethylphenyl)-glycine ethyl ester, N-chloroacetyl-N-(2-methyl-6-ethylphenyl)-glycine isopropyl ester, (1-methylethyl)-O-methyl-O-(4-methyl-2-nitrophenyl)-phosphoramidothioate, 1,1-dimethylhexahydropyridazinum bromide, dimethylpiperidinium chloride, 1-[2-(2,4-dichlorophenyl)-1,3-dioxolan-2-methyl]imidazole, 3'-(trifluoromethyl)-phthalanilic acid, 3,6-dichloropropicolinic acid, benzyl-3,5-dichloro-2,6-difluoro-4-pyridyl ether, ethyl-N-(2,4-dichlorophenyl)-N-(trifluoromethanesulphonyl)-carbamate, N-(p-chlorophenyl)-N-(trifluoromethanesulphonyl)-carbamate, N-(p-chlorophenyl)-3,4,5,6-tetrahydrophthalimide, tributyl-[(5-chloro-2-thienyl)-methyl]-phosphonium chloride, N-pyrrolidinosuccinamic acid, methyl-3,6-dichloro-o-anisole, ethyl-5-(4-chlorophenyl)-2-H-tetrazol-2-yl acetate, 2-(4-ethylamino-6-methylthio-s-triazin-2-yl)-amino-2-methylpropionitrile, 3-cyclohexyl-(6-dimethylamino)-1-methyl-1,3,5-triazine-2,4-(1H,3H)-dione, 1-(N-ethyl-N-propylcarbamoyl)-3-propyl-sulphonyl-1H-1,2,4-triazole, N-ethyl-N-(2-methyl-2-propenyl)-2,6-dinitro-4-(trifluoromethyl)-benzenamine, 2-ethyl-6-methyl-N-(1'-methyl-2'-methoxyethyl)-chloro-acetanilide, 2-(3-chlorophenoxy)-propionic acid, N-n-propyl-N-cyclopropylmethyl-4-trifluoromethyl-2,6-dinitroaniline, N-benzyl-N-isopropyl-3,5-dimethylbenzamide, N-phenyldiethanolamine-bis(2-methoxy-3,6-dichlorobenzoate), [(3,5,6-trichloro-2-pyridinyl)oxy]-acetic acid, 3,3a-dihydro-2-(p-methoxyphenyl)-8H-pyrazolo-(5,1a)-isoindol-8-one, r-2-ethyl-5-methyl-c-5-(2-methylbenzyloxy)-1,3-dioxane, 3-(1-N-ethoxyamino)-propyliden-6-ethyl-3,4-dihydro-2H-pyran-2,4-dione, N-(5-n-butylsulphonyl-1,3,4-thiadiazolyl)-N,N'-dimethyl urea, 1,1-dimethyl-3-(m-chloro-p-trifluoromethoxyphenyl)-urea, 2,6-dimethyl-N-2'-methoxyethyl-chloracetanilide, 1-(2-α,α-dimethylbenzyl)-3-methyl-3-phenyl urea, 1-(o-fluorophenyl)-3-methyl-5-iminohydantoin, N-methyl-N-2-chlorocyclohexylthio-N'-2-fluorophenyl urea, 1-(3,4-dichlorophenyl)-3-methyl-3-(1-formyloxy-2,2,2-trichloroethyl)-urea, N-methyl-N-cyclohexyldithio-N'-o-fluorophenyl urea, N-carboxymethoxymethyl-2,6-diethyl-chloroacetamide, 6-t-butyl-4,5-dihydro-3-isopropyrimidino-[4,5-c]isothiazol-4-one, 6-t-butyl-4,5-dihydro-3-isopropyrimidino-[5,4-d]isoxazol-4-one, O-(5-chloro-1-isopropyl-1,2,4-triazol-3-yl)-O,O-diethylphosphorothioate, 2,4-dichlorophenyl-3-methoxy-4-nitrophenyl ether, 2-ethyl-5-methyl-5-(2-methylbenzyloxy)-1,3-dioxan, N-(1-ethylpropyl)-2,6-dinitro-3,4-xylidine, hexafluoroacetone trihydrate, methyl-tetrachloro-N-methoxy-N-methylterephthalamate, S,S,S-tributyl phosphorotrithioate, N-sec-butyl-2,6-dinitro-3,4-xylidine, N,N-dimethyl-2-(3,4,5-tribromo-1-pyrazolyl)-propionamide, α-(2,2,2-trichloroethyl)-styrene, 2-isopropyl-5-methyl-5-(2-methylbenzyloxy)1,3-dioxane, 1-[O-methyl-sulphamoyl-1-glycol]-hexahydroazepin, O-(methylsulphamoyl)-N,N-hexamethyleneglycollamide, O-(methylsulphamoyl)-glycol-N-isopropylanilide, O-(methylsulphamoyl)-N-isopropylglycollanilide, isobutyl 2-[4-(4-chlorophenoxy)-phenoxy]-propionate, methyl 2-[4-(2,4-dichlorophenoxy)-phenoxy]-propionate, 6-chloro-2-trifluoromethylimidazo(4,5-b)pyridine, pentachlorophenol, N'-p-chlorophenyl-O,N,N-trimethylisourea, 2-chloro-N-(but-1-yn-3-yl)-acetanilide, 2-bromo-2'-methyl-6'-t-butylacetanilide, 2-bromo-N-(methoxymethyl)-2'-methyl-6'-t-butyl-acetanilide, 2-chloro-N-(ethoxycarbonyloxymethyl)-2',6'-diethyl-acetanilide, O-(isopropylsulphamoyl)-N-(but-1-yn-3-yl)-glycollanilide, ethyleneglycol bis-(trichloroacetate), hexachloroacetone, potassium cyanate, sodium chlorate, sodium metaborate, trichlorobenzyl chloride, undecylenic acid, N-1-ethylpropyl)-3,4-dimethyl-2,6-dinitrobenzeneamine, tris(2-methoxyethoxy)-2'-chloroethylsilane, N-[2,4-dimethyl-5[[(trifluoromethyl)-sulphonyl]-amino]-phenyl]-acetamide, 6-t-butyl-4-isobutylideneamino-3-methylthio-1,2,4-trazin-5(4H)-one, 2[4-(2',4'-dichlorobenzyl)-phenoxy]propionic acid, methyl ester, S-(4-methoxybenzyl-N,N-diethylcarbamothioate, 2-chloro-1-(3-ethoxy-4-nitrophenoxy)-4-trifluoromethylbenzene, 3-(3-chloro-4-trifluoromethoxyphenyl)-1,1-dimethyl urea, N-isobutyl-2-oxoimidazolidine-1-carboxamide, O-ethyl-O-(3-methyl-6-nitrophenyl)-N-sec-butyl-phosphorthioamidoate, N-isobutyl-2-oxo-1-imidazolidene carboxamide, 2,6-dichlorobenzyl (2,2-dimethyl-4-ethyldioxolan-4-yl)methyl ether, 3',5'-binitro-4-(di-n-propylamino)acetophenone, N-chloroacetyl-N-(2,6-diethylphenyl) glycine ethyl ester, 2,3:4,6-di-O-isopropylidene-2-keto-L-gulonate, 1-m-trifluoromethylphenyl-4-dimethylamino-5-chloropyridazone, 4-amino-3-methyl-6-phenyl-1,2,4-triazin-5-(4H)-one, N-(2-methoxy-1-methylethyl)-2'-ethyl-6'-methyl-2-chloroacetanilide, O-(N-phenylcarbamoyl)-propanone oxime, N-(4-methyl-3-(trifluoromethylsulphonylamino)phenyl)acetamide, 2,2,3,3-tetrafluoropropionic acid, (1-methylethyl)-O-methyl-O-(4-methyl-2-nitrophenyl)phosphoramidothioate, N-benzyl-N-isopropyl-3,5-dimethylbenzamide, S-(4-methoxybenzyl)-N,N-diethylcarbamothioate, 2-chloro-6-(2-cyano-1-methylethylamino)-4-cyclopropylamino-s-trazine, 2,2-dimethyl-N-benzyl-N-isopropylpropionamide, 3-[5-(1,1-dimethylethyl)-1,3,4-thiadiazol-2-yl]-4-hyć ɔxy-1-methyl-2-imidazolidinone, N-(3-chloro-4-ethoxyphenyl)-N',N'-dimethylurea, 1-methyl-4-phenylpyridinium chloride, N-[5-(2-chloro-1,1-dimethylethyl)-1,3,4-thiadiazol-2-yl]cyclopropane carboxamide, 4-t-butyl-N-s-butyl-2,6-dinitroaniline, 1,1'-di(diethylcarbamoylmethyl)-4,4'-bipyridylium dichloride, 2-t-butyl-4-(2-chloro-4-(3,3-dimethylureido)phenyl)-1,3,4-oxadiazolin-5-one, 2',6'-dimethyl-N-(2-methoxyethyl)-2-chloroacetanilide, α-[4-(4'-chlorophenoxy)phenoxy]propionic acid isobutyl ester, α-[4-(2',4'-dichlorophenoxy)phenoxy]propionic acid methyl ester, N-ethyl-N-propyl-3-(propylsulphonyl)-1H-1,2,4-triazole-1-carboxamide, tris-(2-methoxyethoxy)-2'-chloroethylsilane, N-ethyl-N-(2-methyl-2-propenyl)-2,6-dinitro-4-(trifluoromethyl)aniline, N-2-chloroethyl(-2,6-dinitro-N-propyl-4-(trifluoromethyl)aniline, methyl N-benzoyl-N-(3-chloro-4-fluorophenyl)-2-aminopropionate, isopropyl N-benzoyl-N-(3-chloro-4-fluorophenyl)-2-aminopropionate, 2,4-dichloro-6-fluorophenyl 4-nitrophenyl ether, N-3-(1',1',2',2'-tetrafluoroethoxy)phenyl-N',N'-dimethylurea, 1-methyl-3-phenyl-5-[3-(trifluoromethyl)phenyl]-4-(1H)-pyridinone, 2-amino-4-isopropylamino-6-chloropyrimidine, 6-t-butyl-4-isobutylideneamino-3-methylthio-1,2,4-triazin-5-(4H)-one, α-(4-chlorophenyl)-α-(1-methylethyl)-5-pyrimidinemethanol, 2-(2,4,5-trichlorophenoxy)ethanol, N-[2,4-dimethyl-5-(((trifluoromethyl)sulphonyl)amino)phenyl]acetamide, 2-chloroethyl-tris(methoxy)silane+α,ω-bis(2-chloroethyl)-α,α,ω,ω-tetramethoxypoly[(2-chloroethyl)methoxy]siloxane, O-ethyl-O-(3-methyl-6-nitrophenyl)-N-s-butylphosphorothioamidate, N-(2'-methoxy-1'-methylethyl)-2'-ethyl-6'-methyl-2-chloro-acetanilide, N-(2-methyl-2-propenyl)-2,6-dinitro-N-propyl-4-(trifluoromethyl) aniline, 2-(4-ethylamino-6-methylthio-s-triazin-2-ylamino)-2-methylpropionitrile, N-(1-phenyl-5-bromo-6-oxopyridazin-4-yl) oxamic acid sodium salt, 1,1,1-trifluoro-N-[2-methyl-4-(phenylsulphonyl)-phenyl]methane sulphonamide, 3-ethoxycarbonylaminophenyl N-phenylcarbamate, ammonium ethyl carbamoylphosphonate, 1-allyl-1-tetrahydrogeranylpiperidinium bromide, N-((4-(dipropylamino)-3,5-dinitrophenyl)sulphonyl)-S,S-dimethylsulphilimine, 2-chloro-N-(1-methyl-2-propynyl)acetanilide, N-(5-butylsulphonyl-1,3,4-thiadiazol-2-yl)-N,N'-dimethylurea, 1-[O-(methylsulphamoyl) glycoloyl]hexahydroazepine, 1,3-dimethyl-1-5-dimethylsulphamoyl-1,3,4-thiadiazol-2-yl)urea, 1-(5-ethylsulphonyl-1,3,4-thiadiazol-2-yl)-1,3-dimethylurea, 1-(5-t-butyl-1,3,4-thiadiazol-2-yl)-1,3-dimethylurea, N-(butoxymethyl)-2-chloro-N-(2-(1,1-dimethylethyl)-6-methylphenyl)acetamide, 3-(3-chloro-4-chlorodifluoromethylthiophenyl)-1,1-dimethylurea, [(3,5,6-trichloro-2-pyridinyl)oxy] acetic acid, 2-[4-(4-trifluoromethylphenoxy)]propionic acid methyl ester, and 3-cyclohexyl-6-(dimethylamino)-1-methyl-s-triazine-2,4-(1H,3H)-dione.

Specific preferred admixture are those of a 1-methyl-2-(1-methylpyridinium-4-yl)-s-triazolo[1,5-a]pyridinium salt, a 6,7-dihydropyrido[1,2-a]pyrido[1',2'-1,5]-s-triazolo[3,4-c] pyrazinedium salt, a 6,7-dihydro-10-methylpyrido[1,2-a]pyrido[1',2'-1,5]-s-triazolo[3,4-c]pyrazinedium salt or an 11-chloro-6,7-dihydropyrido[1,2-a]pyrido[1',2'-1,5]-s-triazolo[3,4-c]pyrazinedium salt with one or more of glyphosate, paraquat, diquat, fluometuron, 2,4-D, 2,4-DB, MCPA, MCPB and 2,4,5-T.

The invention also provides a two-container pack in which one or more compounds of formula I or Ia are provided in a first container and one or more further pesticides, plant growth regulants or fertilizers are provided in a second container, especially in relative proportions as described hereinafter. Desirably, the two-container pack bears or contains instructions, either separate or in conjunction with one of the containers, for mixing the contents of the containers or separately applying the contents thereof.

The ratio of the present compound to the second herbicide may vary over a wide range according to the particular compounds involved and the intended use. In general the ratio of present compound to second herbicide lies in the range 1:90 to 99:1, preferably 1:0.1 to 1:15, more preferably 1:0.2 to 5:1, and especially 1:0.3 to 3:1.

The present compounds may be in admixture with non-phytotoxic oils, e.g. Agri-Oil Plus or Sun Oil 11E.

The present compounds are usually employed at a rate of from 0.5 to 8 kg per hectare, for example 1 to 4 kg per hectare.

The present compounds may be applied to plants, the soil, land or aquatic areas. They are preferably used as herbicides, particularly selective herbicides, especially for selectively combating momocotyledonous weeds post-emergence thereof by application to a locus at which a crop e.g. cotton or a food crop, especially a crop such as rice, peas or beans (e.g. navy beans or soya beans) is growing or is to grow.

The invention is illustrated by the following Examples.

EXAMPLE 1

1-Methyl-2-(1-methylpyridinium-4-yl)-s-triazolo[1,5-a]pyridinium bis(methyl sulphate)

(a) 2-(4-Pyridyl)-s-triazolo[1,5-a]pyridine (Ic)

1-Aminopyridinium chloride (7.9g) was added to potassium hydroxide (6.72g) in water (60 ml). 4-Cyanopyridine (31.2g) was added to ethanol (63 ml). The two solutions were then admixed at room temperature and left for 66 hours. The ethanol was then evaporated off in vacuo, and the residue extracted with chloroform (100 ml). The chloroform extract was dried over magnesium sulphate, filtered, and evaporated in vacuo. Recrystallisation of the product from ethanol gave 2-(4-pyridyl)-s-triazolo[1,5-a]pyridine (6.3g), mp 188°-190° C.

(b) 1-Methyl-2-(1-methylpyridinium-4-yl)-s-triazolo[1,5-a]pyridinium bis(methyl sulphate) (Ia)

Dimethyl sulphate (7.56g) was added to 2-(4-pyridyl)-s-triazolo[1,5-a]pyridine (5.88g) and the mixture was heated slowly to 200° C., maintained at that temperature for 15 minutes, and then cooled. The residue was then triturated with petroleum ether to give a brown solid which was then dissolved in the minimum of methanol. Ether was then added to give an oil which was then triturated with ethanol, yielding 1-methyl-2-(1-methylpyridinium-4-yl)-s-triazolo[1,5-a]pyridinium bis(methyl sulphate) (6.2g) as an off-white solid, mp 135°-140° C.

EXAMPLE 2

8-Ethyl-1,5-dimethyl-2-(1-methylpyridinium-4-yl)-s-triazolo[1,5-a] pyridinium bis(methylsulphate)

The above compound was prepared by a method analogous to that of Example 1, mp 140°-142° C.

EXAMPLE 3

2-(1-Methylpyridinium-4-yl)-s-triazolo[1,5-a]pyridine methyl sulphate (I)

2-(4-Pyridyl)-s-triazolo[1,5-a]pyridine (4.0g) prepared as in Example I stage (a) was dissolved in methanol (20 ml), and dimethyl sulphate (1.30g) was added. The mixture was refluxed for 1 hour, and methanol (20 ml) was added. The mixture was then heated to give a solution, which was left to crystallise to yield 4.9g of 2-(1-methylpyridinium-4-yl)-s-triazolo[1,5-a] pyridine methyl sulphate, m.p. 276°–280° C. (decomp).

EXAMPLE 4

2-(1-Ethoxycarbonylmethylpyridinium-4-yl)-s-triazolo[1,5-a] pyridine bromide (I)

2-(4-Pyridyl)-s-triazolo[1,5-a]pyridine (10.0g), prepared as in Example I stage (a) was added to ethyl bromoacetate (25 ml). The mixture was heated to 100° C. for 1 hour, cooled and diluted with ether (80 ml). The solid which formed was filtered off, washed with ether and dried. Recrystallisation from methanol yielded 13.9g of 2-(1-ethoxycarbonylmethylpyridinium-4-yl)-s-triazolo[1,5-a]pyridine bromide, m.p. 174°–176° C.

EXAMPLE 5

2-(1-(Cyanomethyl)pyridinium-4-yl)-s-triazolo[1,5-a]pyridine bromide

The above compound was prepared by a method analogous to that of Examples 3 and 4, mp 254°–256° C. decomp.

EXAMPLE 6

1-Methyl-2-(1-ethoxycarbonylmethylpyridinium-4-yl)-s-triazolo[1,5-a]pyridinium bromide methyl sulphate (Ia)

2-(1-Ethoxycarbonylmethylpyridinium-4-yl)-s-triazolo[1,5-a]pyridine bromide (5.0 g), prepared as in Example 4 and dimethyl sulphate (5 ml) were mixed together, heated slowly to 150° C. and kept at that temperature for 30 minutes. The mixture was then cooled and triturated with isopropanol to give an off-white solid. Filtration, washing with ether and drying yielded 5.20 g of 1-methyl-2-(1-ethoxycarbonylmethyl-pyridinium-4- yl)-s-triazolo[1,5-a]pyridinium bromide methyl sulphate, m.p. 156°–158° C.

EXAMPLE 7

1-Methyl-2-(1-(cyanomethyl)pyridinium-4-yl)-s-triazolo[1,5-a]pyridinium diiodide The above compound was prepared by a method analogous to that of Example 6, mp 184°–186° C.

EXAMPLE 8

(a) 2-(2-Pyridyl)-s-triazolo[1,5-a]pyridine (Ic)

To a stirred and cooled solution of N-aminopyridinium chloride (26.1 g) and 2-cyanopyridine (31.2 g) in ethanol (100 ml) was added a solution of sodium hydroxide (8.0 g) in water (50 ml) over a period of one hour. The mixture was then left at room temperature for 72 hours, after which time the ethanol was removed in vacuo and the residue extracted with chloroform. The chloroform extract was dried and evaporated. The residue, on recrystallisation from acetone, yielded 14.3 g of 2-(2-pyridyl)-s-triazolo[1,5-a]pyridine.

(b) 6,7-Dihydropyrido[1,2-a]pyrido[1',2'-1,5]-s-triazolo[3,4-c]pyrazinediium dibromide (Ia)

2-(2-pyridyl)-s-triazolo[1,5-a]pyridine (5.0 g) was added to 1,2-dibromoethane (25 ml), and the mixture was refluxed with stirring for 3½ hours. The mixture was then cooled, and the solid filtered off, washed with ether and dried. Recrystallisation from methanol yielded 7.6 g of 6,7-dihydropyrido[1,2-a]pyrido[1',2'-1,5]-s-triazolo[3,4-c]pyrazinediium dibromide, mp greater than 310° C.

EXAMPLE 9

11-chloro-6,7-dihydropyrido[1,2-a]pyrido[1',2'-1,5]-s-triazolo[3,4-c]pyrazinediium dibromide (Ia)

The above compound was prepared by a method analogous to that of Example 8, mp >300° C.

EXAMPLE 10

(a) N-(4-chloro-2-pyridyl)pyridine-2-carboxamide (III)

5-chloro-2-aminopyridine (25.7 g) and 2-cyanopyridine (20.8 g) were added to methanol (60 ml), and the mixture was treated with sodium methoxide (1 g) in methanol (20 ml). It was then left overnight, and glacial acetic acid (4 ml) was added. The mixture was refluxed for 5 hours, then cooled, and the solid was filtered off. Evaporation of the filtrate yielded further product (32.7 g) mp 118°–120° C.

(b) 2-(2-Pyridyl)-6-chloro-s-triazolo[1,5-a]pyridine (Ic)

N-(4-chloro-2-pyridyl)pyridine-2-carboxamide (23.25 g) prepared as in stage (a) was dissolved in methanol (200 ml), and IN hydrochloric acid (100 ml) was added. The mixture was then cooled in ice, and sodium hypochlorite solution (67.5 ml, 1.56 M). The mixture was then stirred for five minutes and sodium carbonate (13.8 g) in the minimum of water was added. The mixture was then refluxed for 20 minutes and cooled to give a solid which was filtered off. Evaporation of the filtrate gave a further yield of product (17.2 g), mp 118°–119° C.

(c) 11-Chloro-6,7-dihydropyrido[1,2-a]pyrido[1',2'-1,5]-s-triazolo[3,4-c]pyrazinediium dibromide (Ia)

The product of stage (b) (5.0 g) was added to dibromoethane (25 ml) and the mixture was refluxed for 1 hour, cooled, and the solid which formed filtered off. It was then washed with dichloroethane, then ether, and finally dried in vacuo. Yield 6.1 g, mp >300° C.

EXAMPLES 11–14

The following compounds were prepared by methods analogous to that of Example 10.

11. 6,7-dihydro-10-methylpyrido[1,2-a]pyrido[1',2'-1,5]-s-triazolo[3,4-c]pyrazinediium dibromide, mp >300° C.

12. 6,7-dihydro-10,12-dimethylpyrido[1,2-a]pyrido[1',2'-1,5]-s-triazolo[3,4-c]pyrazinediium dibromide, mp 334°–340° C.

13. 11-bromo-6,7-dihydro-12-methylpyrido[1,2-a]pyrido[1',2'-1,5]-s-triazolo[3,4-c]pyrazinediium dibromide, mp >300° C.

14. 7,8-dihydro-6H-pyrido[1,2-a]pyrido[1',2'-1,5]-s-triazolo[3,4-c]-1,4-diazepinediium dibromide, mp 280°–282° C.

EXAMPLE 15

7,10-Dimethylpyrido[1,2-a]pyrido[1',2'-1,5]-s-triazolo[3,4-c]pyrazinediiumdichloride 2-(2-Pyridyl)-7-methyl-s-triazolo[1,5-a]pyridine (10 g) was added to chloroacetone (30 ml) and the mixture was refluxed for 2 hours. The mixture was cooled, and ether (100 ml) was added. The solid was filtered off, washed with ether, and dried in vacuo to give 1-acetonyl-2-(7-methyl-s-triazolo[1,5-a]pyridin-2-yl)pyridinium chloride. The product was then added to phosphorus trichloride (25 ml) and refluxed for 30 minutes, then cooled, and ether (100 ml) was added. The solid was filtered off, washed with ether, and dried in vacuo, to give 6.8 g of 7,10-dimethyl-pyrido[1,2-a]pyrido[1',2'-1,5]-s-triazolo[3,4-c]pyrazinedium dichloride, mp 186°–188° C.

EXAMPLE 16

Seeds of various weed species as set out in the Table below were sown in anodised aluminum pans 19 cm×9.5 cm×5.0 cm containing John Innes I potting compost. They were then watered and placed in a controlled environment room (22° C.; 65–85% RH; 14 hours artificial illumination at 1600 foot-candles). 14 Days after sowing, the seedlings were given a foliar spray of the compound of Example 1, 8(b), 9 and 11, formulated as an aqueous solution containing 1000 ppm of the wetting agent Lissapol NX (condensation product of nonylphenol and ethylene oxide). The dosage rate was adjusted to apply 2.8 kg of active ingredient in 450 liters/hectare.

After a further 14 days in the controlled environment room, the plants were visually assessed for any growth regulatory or herbicidal effect. All differences from an untreated control were scored on a scale 0–100 where 0 signifies no effect and 100 signifies complete suppression.

The results in % kill are as set out in the following Table.

| Species | Example No. | | | |
|---|---|---|---|---|
| | 1 | 8(b) | 11 | 9 |
| Wheat (*Triticum aestivum*) | 65 | 90 | 45 | 75 |
| Barley (*Hordeum vulgare*) | 40 | 95 | 50 | 45 |
| Wild Oats (*Avena fatua*) | 35 | 35 | 25 | 10 |
| Blackgrass (*Alopecurus myosuroides*) | 30 | 65 | 30 | 10 |
| Barnyardgrass (*Echinochloa crus-galli*) | 100 | 100 | 95 | 100 |
| Crabgrass (*Digitaria sanguinalis*) | 100 | 100 | 95 | 100 |
| Pigweed (*Amoranthus retroflexus*) | 100 | 100 | 100 | 100 |
| Yellow nutsedge (*Cyperus esculentus*) | 80 | 90 | 80 | 90 |
| Purple nutsedge (*Cyperus rotundus*) | 90 | 70 | 50 | 90 |
| Couch (*Agropyron repens*) | 90 | 80 | — | 50 |
| Foxtail Millet (*Setaria italica*) | 100 | — | — | — |
| Yellow Foxtail (*Setaria lutescens*) | 100 | — | — | — |
| Common Millet (*Panicum miliaceum*) | 100 | — | — | — |
| Johnson Grass (*Sorghum halepense*) | 100 | — | — | — |
| Chickweed (*Stellaria media*) | — | 100 | 70 | 95 |
| Mayweed (*Matricaria* spp) | — | 100 | 50 | 100 |
| Cleavers (*Galium aparine*) | — | 65 | 5 | 45 |
| Fathen (*Chenopodium album*) | — | 90 | 50 | 100 |
| Corn marigold (*Chrysanthemum segetum*) | — | 100 | 90 | 100 |
| Pale persicaria (*Polygonum lepathifolium*) | — | 90 | 50 | 100 |

EXAMPLE 17

Seeds of Peas, Mustard, Linseed, Ryegrass, Sugarbeet, Oats and French beans were sown in anodised aluminium pans, 19 cm long ×9.5 cm wide×5 cm deep containing John Innes I potting compost. They were then watered and placed in a controlled environment room (22° C.; 65–85% RH; 14 hours artificial illumination at 1200 foot candles). Fourteen days after sowing the seedlings received a foliar spray of the compounds of Examples 1, 8(b), 9 and 11, formulated as an aqueous solution together with 1000 ppm of the wetting agent Lissapol NX. The concentrations of active ingredient and volume of application were adjusted so as to be equivalent to rates of 11.2, 2.8 and 0.7 kg/ha in 450 liters per hectare.

After 7 days growth in the controlled environment room the plants were visually assessed for any herbicidal or growth regulant response. All differences from the untreated control were scored according to a herbicidal index where 0=no effect and 100=complete kill.

The results in % kill are as set out in the following table:

| Species Dosage rate kg/ha- | Example 1 | | | Example 8(b) | | Example 11 | | Example 9 | |
|---|---|---|---|---|---|---|---|---|---|
| | 11.2 | 2.8 | 0.7 | 11.2 | 2.8 | 11.2 | 2.8 | 11.2 | 2.8 |
| Peas (*Pisum sativum*) | 25 | 10 | 5 | 60 | 20 | 65 | 30 | 65 | 30 |
| Mustard (*Sinapis alba*) | 35 | 5 | 0 | 85 | 10 | 35 | 25 | 65 | 40 |
| Linseed (*Linum usitatissimum*) | 85 | 25 | 5 | 100 | 100 | 100 | 80 | 100 | 100 |
| Ryegrass (*Lolium perenne*) | 100 | 65 | 15 | 100 | 100 | 100 | 90 | 100 | 100 |
| Sugarbeet (*Beta vulgaris*) | 100 | 100 | 100 | 100 | 100 | 100 | 100 | 100 | 100 |
| Oat (*Avena sativa*) | 95 | 35 | 10 | 90 | 70 | 65 | 25 | 50 | 25 |
| French beans (*Phaseolus vulgaris*) | 25 | 15 | 5 | 90 | 70 | 65 | 40 | 100 | 50 |

EXAMPLE 18

An aqueous solution was prepared containing 429 grams per liter of the compound of Example 8 (b), equivalent to 25% by weight of the cation. On dilution of this solution with water and application to a crop of soya beans at a rate of 2.8 kg/ha in 450 l/ha, excellent weed control was observed with no apparent damage to the crop.

EXAMPLE 19

An aqueous solution was prepared containing 405 grams per liter of the compound of Example 9, equivalent to 25% by weight of the cation. On suitable dilution of this solution with water and application to cotton plants at a rate of 2.8 kg/ha in 450 l/ha, excellent weed control was observed with no apparent damage to the crop.

We claim:

1. A compound of formula Ia:

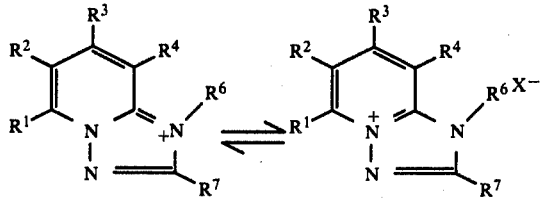

wherein
R¹, R², R³ and R⁴, which may be the same or different, each represent hydrogen; C 1 to 6 alkyl which is unsubstituted or substituted by a halogen atom; phenyl or C 7 to 10 phenylalkyl each of which may be unsubstituted or substituted by a halogen atom or by a C 1 to 6 alkyl group; nitro; cyano; or halogen;

X⁻ represents an anion;

R⁷ represents a pyridinium-2-yl group which is unsubstituted or substituted by a C 1 to 6 unsubstituted alkyl group or a C 1 to 6 alkyl group which is itself substituted by a cyano, carboxy or C 1 to 6 alkoxycarbonyl group;

and R⁶ represents a methylene, dimethylene, trimethylene or a C 1 to 6 alkyl substituted ethenylene chain to the nitrogen atom of the group R⁷.

2. A compound according to claim 1 wherein at least two of R¹, R², R³ and R⁴ represent hydrogen.

3. A compound according to claim 1 wherein at least one of R¹, R², R³ and R⁴ represents halogen.

4. A compound according to claim 1 wherein at least one of R¹, R², R³ and R⁴ represents the substituted or unsubstituted C 1 to 6 alkyl group.

5. A compound according to claim 1 wherein X⁻ represents Cl⁻, Br⁻, I⁻ or CH₃SO₄⁻.

6. A 6,7-dihydropyrido[1,2-a]pyrido[1¹,2¹-1,5]-s-triazolo[3,4-c]pyrazinediium salt.

7. A 6,7-dihydro-10-methylpyrido[1,2-a]pyrido[1¹,2¹-1,5]-s-triazolo[3,4-c]pyrazinediium salt.

8. An 11-chloro-6,7-dihydropyrido[1,2-a]pyrido[1¹,2¹-1,5]-s-triazolo[3,4-c]pyrazinediium salt.

9. A method of combating weeds at a locus infested with or liable to be infested with weeds, which method comprises applying to said locus a herbicidally-effective amount of one or more compounds of formula Ia according to claim 1.

10. A method according to claim 9 wherein the rate of application of the compounds of formula Ia is from 0.5 to 8 kg per hectare in total.

11. A herbicidal composition which comprises from 0.5 to 85% by weight of one or more compounds of formula Ia according to claim 1 in association with a surface active agent and/or a carrier.

* * * * *